(12) United States Patent
Endou et al.

(10) Patent No.: US 8,236,488 B2
(45) Date of Patent: Aug. 7, 2012

(54) METHOD OF SCREENING FOR THERAPEUTIC COMPOUNDS FOR VASCULAR DISORDERS AND HYPERTENSION BASED ON URAT1 ACTIVITY MODULATION

(75) Inventors: Hitoshi Endou, Kanagawa (JP); Yoshikatsu Kanai, Tokyo (JP); Richard J. Johnson, Gainesville, FL (US); Karen L. Price, Dyfed (GB)

(73) Assignee: Human Cell Systems, Inc., Tokyo (JP)

( * ) Notice: Subject to any disclaimer, the term of this patent is extended or adjusted under 35 U.S.C. 154(b) by 871 days.

(21) Appl. No.: 10/579,173

(22) PCT Filed: Nov. 11, 2004

(86) PCT No.: PCT/JP2004/016761
§ 371 (c)(1),
(2), (4) Date: Dec. 4, 2008

(87) PCT Pub. No.: WO2005/046724
PCT Pub. Date: May 26, 2005

(65) Prior Publication Data
US 2009/0312415 A1 Dec. 17, 2009

(30) Foreign Application Priority Data
Nov. 14, 2003 (JP) ................. 2003-384863

(51) Int. Cl.
*C12Q 1/62* (2006.01)
*C07K 14/47* (2006.01)
(52) U.S. Cl. .............. 435/4; 436/12; 514/15.7
(58) Field of Classification Search .......... None
See application file for complete search history.

(56) References Cited

FOREIGN PATENT DOCUMENTS

| | | |
|---|---|---|
| CA | 2456172 | 4/2003 |
| EP | 1 428 880 A1 | 6/2004 |
| GB | 1493237 | 11/1977 |
| JP | 2003-094067 A | 4/2003 |
| WO | WO-02/00210 A2 | 1/2002 |

OTHER PUBLICATIONS

Kanellis et al., Uric Acid Stimulates Monocyte Chemoattractant Protein-1 Production in Vascular Smooth Muscle Cells Via Mitogen-Activated Protein Kinase and Cyclooxygenase-2, Hypertension, 41, 1287-1293, 2003.*
Hurteau et al., Transforming growth factor beta inhibits proliferation of human ovarian cancer cells obtained from ascites, Cancer, 74, 93-99, 1994.*
Enomoto et al., Nature, 417:447-452 (2002).
Enomoto et al., "Urate Transporter and REnal Hypouricemia", RBYOAI, 51(9):827-950 (2003).
Yokoyama et al., Molecular Medicine, 40(7):762-768 (2003).
Endo et al., Pharmacia, 39(5):431-435 (2003).
Chikako Ogawa et al., "Stereospecific, Enantioselective Allylation of α-Hydrazono Esters by Using Allyltrichlorosilanes with BINAP Dioxides as Neutral-Coordinate Organocatalysts", Angewandte Chemie, International Edition, 43(47), pp. 6491-6493 (2004).
Chikako Ogawa et al., "Phosphine Oxides as Efficient Neutral Coordinate-Organocatalysts for Stereoselective Allylation of N-acylhydrazones", Organic & Biomolecular Chemistry, 2(4), pp. 446-448 (2004).
Database WPI Week 200382, Derwent Publication Ltd., London, GB; XP-002464497; AN 2003-884288 (Sep. 25, 2003).

* cited by examiner

*Primary Examiner* — Elly-Gerald Stoica
(74) *Attorney, Agent, or Firm* — Edwards Wildman Palmer LLP; Peter F. Corless

(57) ABSTRACT

It is intended to clarify a transportation system participating in the uric acid uptake in vascular smooth muscle cells (VSMCs) and provide a novel remedy, a preventive or a treating agent for vascular disorders, hypertension and renal disorders with the use of a drug participating in this transportation system. It is also intended to provide a novel screening system for a remedy, a preventive or a treating agent for vascular disorders, hypertension and renal disorders with the use of such a transportation system. Namely, a medicinal composition for healing, preventing or treating vascular disorders, hypertension and renal disorders which comprises a drug having an effect of inhibiting the uric acid uptake by a uric acid transporter URAT1 and a pharmaceutically acceptable carrier; and a method of screening a substance efficacious for healing, preventing or treating vascular disorders, hypertension and renal disorders which comprises using a cell line expressing URAT1 in the presence or absence of a test compound and assaying the uric acid uptake level, cell proliferation ability or the amount of a monocyte chemotactic factor produced by the cells.

4 Claims, 9 Drawing Sheets

SEQUENCE LISTING

<160> NUMBER OF SEQ ID NOS: 10

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgtgcagcc tatgcaccca actatac                                        27

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctttgctta gagtcagttc cttctgcag                                      29

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccatcaacta catcatgttc gtagtcaccc g                                   31

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatatgtcgg agctgagatg ttcggaacag                                     30

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagacaccat tgtgatagag tgggacttg                                      29

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 6
gatagaacca gccagcgtat ggactctggt ac                                    32

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catcttatgc ttatccggga caagtcctc                                        29

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagtctgttg aagagggtag agcagtctac                                       30

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acccccaatg tatccgttgt                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tactccttgg aggccatgta                                                  20
```

METHOD OF SCREENING FOR THERAPEUTIC COMPOUNDS FOR VASCULAR DISORDERS AND HYPERTENSION BASED ON URAT1 ACTIVITY MODULATION

The present application is a national stage entry of PCT/JP2004/016761, filed Nov. 11, 2004.

TECHNICAL FIELD

The present invention relates to a medicinal composition for healing, preventing or treating vascular disorders, hypertension, and renal disorders, which comprises a drug having the effect of inhibiting uric acid uptake by URAT1 and a pharmaceutically acceptable carrier. Further, the present invention relates to a method of screening a substance efficacious for healing, preventing or treating vascular disorders, hypertension, and renal disorders, which comprises using a cell line expressing URAT1 in the presence or absence of a test compound and assaying the uric acid uptake level, the proliferation ability of the cells and/or the amount of a monocyte chemotactic factor produced by the cells.

BACKGROUND ART

It has been considered that hyperuricemia (increase in serum uric acid level) is deeply related to hypertension, renal disorders, and cardiovascular disorders. Because people with high uric acid levels have well known risk factors associated with cardiovascular disorders, it has been considered, based on such an epiphenomenon, that there is a relation between these risk factors and uric acid. In order to clarify the relation between risk factors associated with hypertension, renal disorders, and cardiovascular disorders and uric acid, immunological studies have been carried out by, for example, a multivariate analysis using other risk factors as controls.

The present inventors have developed rat models with mild hyperuricemia by administering a uricase inhibitor such as oxonic acid to rats. Interestingly, these hyperuricemic rat models develop hypertension, glomerular vascular disorders, and renal disorders (see Non-Patent Documents 1 to 6). It has been considered that the mechanism is not mediated by intra-renal crystal deposition, but instead involves activation of renin-angiotensin system and inhibition of nitric oxide synthase in macula densa (which is a group of cells that is densely packed in distal tubular epithelium, and strongly stained, and is in direct contact with juxtaglomerular cells) (see Non-Patent Documents 1 and 2). Further, the present inventors have reported that such vascular disorders occur independently of blood pressure (see Non-Patent Document 2).

Based on the finding that hyperuricemia induces vascular disorders independently of blood pressure, the effect of uric acid on vascular smooth muscle cells (VSMCs) has been examined. Rao et al. have reported that uric acid stimulated the expression of platelet-derived growth factor (PDGF) A-chain and rat VSMC cell proliferation (see Non-Patent Document 7). Further, the present inventors have shown that this pathway involves activation of expression of specific mitogen-activated protein kinase (MAP Kinase) (ERK), cyclooxygenase-2 (COX-2), PDGF A- and B-chains, and PDGF-α receptor mRNA (see Non-Patent Documents 2 to 4). Furthermore, the present inventors have shown that uric acid stimulates the expression of a monocyte chemotactic factor (MCP-1) in VSMCs, and that hyperuricemia stimulates vascular smooth muscle to promote cell proliferation and induce production of inflammatory cytokine (see Non-Patent Document 8).

However, a major question arises as to how uric acid enters VSMCs to induce these events. No receptor for uric acid has been known. Further, since uric acid is a water-soluble material, involvement of any transporter is absolutely necessary to allow uric acid to pass through cell membrane and enter smooth muscle cells.

Studies in renal cells have shown that urate transporters likely include both an organic anion transporter/exchanger (OAT family) and a voltage-sensitive channel (see Non-Patent Documents 9 to 11). Further, it has been shown that some members of OAT family, especially OAT1 and OAT3 (via basolateral membrane) and URAT1 (via luminal membrane) mediate urate uptake in renal cells (see Non-Patent Documents 12 to 15). Furthermore, a voltage-sensitive channel/transporter mechanism has been shown, and a putative transporter (UAT) has been identified (see Non-Patent Documents 16 to 18). However, no study has been made to determine which channels/transporters are expressed in rat VSMCs and whether they function or not. Further, it has not been known that what kind of material functions as a urate transporter in VSMCs.

The present inventors have identified a novel clone (URAT1) by a 3'-RACE method using human kidney cell mRNA. This urate transporter URT1 (urate transporter 1) has the ability to transport uric acid and its analogs from one side to the other side via cell membrane, and is an exchange transporter (urate/anion exchanger) that allows the anion at the other side of cell membrane to be an exchange substrate (see Patent Document 1).

The following prior art documents related to the present invention are incorporated herein by reference.

Patent Document 1: Japanese Patent Application Laid-open No. 2003-93067
Non-Patent Document 1: Mazzali M, Hughes J, et al., Hypertension, 2001; 38, 1101-1106
Non-Patent Document 2: Mazzali M, Kanellis J, et al., Am. J. Physiol. Renal Physiol., 2002; 282, F991-997
Non-Patent Document 3: Watanabe S, Kang D H, et al., Hypertension, 2002; 40, 355-360
Non-Patent Document 4: Kang D H, Nakagawa T, et al., J. Am. Soc. Nephrol., 2002; 13, 2888-2897
Non-Patent Document 5: Nakagawa T, Mazzali M, et al., Am. J. Nephrol., 2003; 23, 2-7
Non-Patent Document 6: Sanchez-Lozada L G, Tapia E, et al., Am. J. Physiol. Renal Physiol., 2002; 283, F1105-F1110
Non-Patent Document 7: Rao G N, Corson M A, et al., J. Biol. Chem., 1991; 266, 8604-8608
Non-Patent Document 8: Kanellis J, Watanabe S, et al., Hypertension, 2003; 41, 1287-1293
Non-Patent Document 9: Roch-Ramel F, Guisan B, et al., J. Pharm. Exp. Ther., 1997; 280, 839-845
Non-Patent Document 10: Roch-Ramel F, Werner D, et al., Am. J. Physiol. Renal Physiol., 1994; 266, F797-F805
Non-Patent Document 11: Knorr B A, Beck J C, et al., Kidney Int., 1994; 45, 727-736
Non-Patent Document 12: Sekine T, Cha S H, et al., Eur. J. Physiol., 2000; 440, 337-350
Non-Patent Document 13: Cha S H, Sekine T, et al., Mol. Pharmacol., 2001; 59, 1277-1286
Non-Patent Document 14: Kimura H, Chairoungdua A, et al., Nature, 2002; 417, 447-452
Non-Patent Document 15: Motohashi H, Sakurai Y, et al., J. Am. Soc. Nephrol., 2002; 13, 866-874

Non-Patent Document 16: Leal-Pinto E, Cohen B E, et al., J. Membrane. Biol., 1999; 169, 13-27

Non-Patent Document 17: Leal-Pinto E, Tao W, et al., J. Biol. Chem., 1997; 272, 617-625

Non-Patent Document 18: Lipkowitz M S, Leal-Pinto E, et al., J. Clin. Invest., 2001; 107, 1103-1115

DISCLOSURE OF THE INVENTION

Problems to be Solved by the Invention

It is an object of the present invention to clarify a mechanism of uric acid uptake into vascular smooth muscle cells (VSMCs) and a transportation system participating in uric acid uptake, and to provide a novel remedy, preventive or treating agent for vascular disorders, hypertension, and renal disorders with the use of a drug participating in the transportation system. It is another object of the present invention to provide a novel system for screening a remedy, preventive or treating agent for vascular disorders, hypertension, and renal disorders with the use of the transportation system.

Means for Solving the Problems

It has been hitherto considered that urate transporter URAT1 is expressed only in kidney. However, the present inventors have experimentally demonstrated that URAT1 is expressed also in vascular smooth muscle cells at both RNA level and protein level. In transportation of uric acid from blood to smooth muscle cells, URAT1 plays an important role as a urate transporter in the smooth muscle cells. More specifically, although it has already known that URAT1 is present on the luminal side of proximal renal tubule and has the function of reabsorbing uric acid to regulate blood uric acid level, it has been shown that URAT1 is present also in vascular smooth muscle cells and participates in transportation of uric acid from blood to smooth muscle cells, and that such action plays an important role in development of morbid conditions such as hypertension and vascular lesions induced by hyperuricemia. These findings have shown that a drug having the effect of inhibiting uric acid uptake via URAT1, such as a URAT1 inhibitor or blocker is efficacious for healing, preventing or treating vascular disorders, hypertension, and renal disorders, more specifically those induced by hyperuricemia. As described above, since it has been shown that formation of vascular lesions induced by hyperuricemia is mediated by URAT1, it becomes possible to develop a novel antihypertensive and a novel drug that exerts a vascular protective effect by inhibiting blood vessel degeneration, with the use of a cell line stably expressing URAT1 gene.

The present invention relates to a medicinal composition for healing, preventing or treating vascular disorders, hypertension, and renal disorders, more specifically those induced by hyperuricemia, which comprises a drug having the effect of inhibiting uric acid uptake via URAT1, such as a URAT1 inhibitor or blocker; and a pharmaceutically acceptable carrier.

Further, the present invention relates to a method of screening a substance efficacious for healing, preventing or treating vascular disorders, hypertension, and renal disorders, which comprises using a cell line expressing URAT1, such as a cell line stably expressing URAT1 gene in the presence or absence of a test compound; and assaying the uric acid uptake level.

Furthermore, the present invention relates to a method of screening a substance efficacious for healing, preventing or treating vascular disorders, hypertension, and renal disorders, which comprises using a cell line expressing URAT1, such as a cell line stably expressing URAT1 gene in the presence or absence of a test compound; and assaying the proliferation ability of the cells.

Moreover, the present invention relates to a method of screening a substance efficacious for healing, preventing or treating vascular disorders, hypertension, and renal disorders, which comprises using a cell line expressing URAT1, such as a cell line stably expressing URAT1 gene in the presence or absence of a test compound; and assaying the amount of a monocyte chemotactic factor produced by the cells.

First, the present inventors examined urate uptake into vascular smooth muscle cells (VSMCs).

Urate uptake into vascular smooth muscle cells (VSMCs) was examined under polarized and depolarized conditions. The $^{14}$C-urate uptake level by VSMCs was measured using an uptake solution containing 20 μM $^{14}$C-urate under polarized conditions (HEPES-physiological saline solution) or depolarized conditions (100 mM KCl uptake solution) for 120 minutes. The $^{14}$C-urate uptake level was measured every one minute. Each of the measurement results is the average±standard deviation of three wells. The result is shown in FIG. 1. In FIG. 1, a vertical axis represents the $^{14}$C-urate uptake (CPM) level, a horizontal axis represents time (min), the symbol "☐" represents a case where urate uptake was examined under depolarized conditions, and the symbol "◆" represents a case where urate uptake was examined under polarized conditions. In FIG. 1, an asterisk (*) indicates that there is a significant difference ($p<0.05$). It can be known that urate is rapidly taken up by rat VSMCs, that under depolarized conditions, urate uptake reaches steady state within about 15 minutes, and that under polarized conditions, urate uptake reaches steady state within about 30 minutes. In addition, the urate uptake level is larger under depolarized conditions than under polarized conditions all the time. This result indicates that urate is taken up by VSMCs through a conductive pathway.

Further, the present inventors examined a mechanism of urate uptake under physiologic conditions (polarized conditions). First, the present inventors examined whether $^{14}$C-urate competed with cold urate for uptake. The $^{14}$C-urate uptake level by rat VSMCs was measured at 37° C. for 5 minutes using an uptake solution containing 20 μM $^{14}$C-urate and 0, 0.1, 1, 5, 10, or 50 mg/dL cold urate. Each of the measurement results is the average±standard deviation of three wells. The result is shown in FIG. 2. FIG. 2 shows the result of the test carried out to examine competition between $^{14}$C-urate and cold urate for uptake by rat VSMCs. In FIG. 2, a vertical axis represents the ratio (%) of $^{14}$C-urate uptake level determined when the $^{14}$C-urate uptake level in the absence of cold urate is defined as 100%. A horizontal axis represents the concentration of cold urate (mg/dL). In FIG. 2, an asterisk (*) indicates that there is a significant difference ($p<0.05$). As a result, it is known that $^{14}$C-urate more effectively competed with cold urate for uptake by rat VSMCs for 5 minutes at a higher concentration of cold urate. This indicates that urate uptake into VSMCs is at least partially carried out by a transportation system.

A specific receptor for uric acid is hitherto unknown. Therefore, it can be considered that uric acid uptake is carried out via some kind of transporter. It has been already reported that several kinds of urate transporters are present in kidney. In addition, it has been already reported that uric acid uptake in renal cells is mediated by a voltage-sensitive pathway and organic anion exchange (see Non-Patent Documents 9 to 11). The fact that the urate uptake level into depolarized cells is larger (see FIG. 1) indicates the presence of a voltage-sensitive transporter.

It has been already proved that urate uptake in renal tubular epithelial cells is mediated by transportation via organic anion transportation systems. For example, it has been already reported that on the luminal membrane, urate uptake is mediated by URAT1 (see Non-Patent Document 13) and that on the basolateral membrane, urate uptake is mediated by OAT1 and OAT3 (see Non-Patent Document 14). These protein-mediated transportation systems can be inhibited by probenecid or benzbromarone.

In order to determine the presence of organic anion transporters, a test was carried out to examine whether $^{14}$C-urate uptake into rat VSMCs was concentration-dependently inhibited by an inhibitor of transporter-mediated urate uptake, namely, probenecid or benzbromarone. The $^{14}$C-urate uptake level was measured at 37° C. for 5 minutes using an uptake solution containing 20 μM $^{14}$C-urate and 0, 0.1, 0.5 or 1 mM probenecid or 0, 0.5, 1 or 10 μM benzbromarone. Each of the measurement results is the average±standard deviation of three wells. The result is shown in FIGS. 3 and 4. FIG. 3 shows the result of the test carried out to examine the effect of probenecid on $^{14}$C-urate uptake inhibition and FIG. 4 shows the result of the test carried out to examine the effect of benzbromarone on $^{14}$C-urate uptake inhibition. In FIGS. 3 and 4, a vertical axis represents the ratio (%) of $^{14}$C-urate uptake level determined when the $^{14}$C-urate uptake level in the absence of probenecid (FIG. 3) or benzbromarone (FIG. 4) is defined as 100%. A horizontal axis in FIG. 3 represents the concentration of probenecid (mM), and a horizontal axis in FIG. 4 represents the concentration of benzbromarone (μM). An asterisk (*) in the FIGS. 3 and 4 indicate that there is a significant difference (p<0.05)

Further, another test was carried out to examine whether $^{14}$C-urate competed with an organic anion such as para-amino hippurate (PAH) or lactate for uptake. The $^{14}$C-urate uptake level by rat VSMCs was measured at 37° C. for 5 minutes using an uptake solution containing 20 μM $^{14}$C-urate and 0, 100, 250 or 500 μM PAH or 0, 100, 250 or 500 lactate. In addition, the $^{14}$C-urate uptake level by rat VSMCs was also measured using an uptake solution containing 20 μM $^{14}$C-urate and 250 μM uric acid (UA). Each of the measurement results is the average±standard deviation of three wells. The result is shown in FIGS. 5 and 6. FIG. 5 shows the result of the test carried out to examine the competition between $^{14}$C-urate and PAH for uptake and FIG. 6 shows the result of the test carried out to examine the competition between $^{14}$C-urate and lactate for uptake. In FIGS. 5 and 6, a vertical axis represents the ratio (%) of $^{14}$C-urate uptake level determined when the $^{14}$C-urate uptake level in the absence of PAH (FIG. 5) or lactate (FIG. 6) is defined as 100%. A horizontal axis in FIG. 5 represents the concentration of PAH (μM), and a horizontal axis in FIG. 6 represents the concentration of lactate (μM). An asterisk (*) in FIGS. 5 and 6 indicate that there is a significant difference (p<0.05).

The result shown in FIGS. 5 and 6 indicates the presence of organic anion transporters having an affinity for urate, lactate, and PAH in VSMCs.

As described above, uric acid uptake into VSMCs is concentration-dependently reduced by probenecid or benzbromarone that is well known as an inhibitor of organic anion transporter (OAT) family. Further, uric acid uptake into VSMCs is inhibited in the presence of PAH, and is more weakly inhibited in the presence of lactate. Therefore, it can be considered that uric acid transportation system in VSMCs has an affinity for a substrate such as PAH or lactate. Like cells, VSMCs are electronegative to extracellular fluid. The membrane potential is advantageous for transportation of uric acid via a voltage-sensitive transporter. However, an actual electrochemical driving force for uric acid uptake is unknown because intracellular uric acid concentrations have not been measured.

Next, the present inventors examined whether an inhibitor of organic anion transportation inhibited the response of VSMC proliferation. Proliferation of VSMCs after 24 hour incubation was determined by measuring the $^3$H-thymidine uptake level. This test was carried out for cases where no uric acid (UA) was present, 3 mg/dL uric acid (UA) was present, 3 mg/dL uric acid and 0.1, 0.5 or 1 mM probenecid were present, and 3 mg/dL uric acid (UA) and 0.5, 1 or 10 μM benzbromarone were present. In addition, the test was also carried out for cases where probenecid was present alone and benzbromarone was present alone. Each of the measurement results is the average±standard deviation of three wells (CPM). FIGS. 7 and 8 show the result of the test carried out to examine the effect of probenecid (FIG. 7) or benzbromarone (FIG. 8) on inhibition of response of VSMC proliferation. In FIGS. 7 and 8, a vertical axis represents the $^3$H-thymidine uptake (CPM) level, a horizontal axis represents the concentration of uric acid or the concentration of an inhibitor. Two asterisks (**) in FIGS. 7 and 8 indicate that there is a significant difference (p<0.05) when compared to a case where no stimulator is present, and a single asterisk (*) indicates that there is a significant difference (p<0.05) when compared to a case where 3 mg/dL uric acid is present.

As shown in FIG. 7, uric acid (UA) increased the $^3$H-thymidine uptake level by rat VSMCs, and a uric acid-induced increase in the $^3$H-thymidine uptake level was concentration-dependently inhibited in the presence of probenecid. In the absence of uric acid and the presence of probenecid alone, probenecid had little effect on cell proliferation. The same was observed also in the case of benzbromarone (see FIG. 8).

A comparison was made between the ratio (%) of cell proliferation inhibition by an inhibitor of organic anion transportation after 24 hour incubation and the ratio (%) of uric acid uptake inhibition by an inhibitor of organic anion transportation for 5 minutes. Each of the inhibition rates (%) was determined based on a case where no inhibitor was used (100%). The ratio of cell proliferation inhibition and the ratio of uric acid uptake inhibition were determined using the same concentrations of an inhibitor, and were plotted to obtain a graph. FIG. 9 shows a result obtained using probenecid as an inhibitor. In FIG. 9, a vertical axis represents the ratio of VSMC proliferation inhibition (%), and a horizontal axis represents the ratio of uric acid uptake inhibition (%) As a result, it has been found that there is a correlation between these inhibition ratios. In a case where probenecid was used as an inhibitor, the correlation coefficient r between them was 0.95 (see FIG. 9), and in a case where benzbromarone was used as an inhibitor, the correlation coefficient r between them was 0.98.

The present inventors have already reported that uric acid induces the production of MCP-1 (see Non-Patent Document 8). The production of MCP-1 in VSMC was examined. Rat VSMCs were cultured for 24 hours, and the amount of MCP-1 secreted into culture supernatant was measured by ELISA. A test was carried out for cases where 3 mg/dL uric acid (UA) was present, 3 mg/dL uric acid and 1 mM probenecid were present, and probenecid was present alone. The result is shown in FIG. 10. In FIG. 10, a vertical axis represents the amount of MCP-1 (pg/1000 cells), and a horizontal axis represents cases where nothing was present (No UA), 3 mg/dL uric acid was present (UA), 3 mg/dL uric acid and 1 mM probenecid were present (UA+Prob), and probenecid was present alone (Prob), and two asterisks (**) indicate that there is a significant difference (p<0.05) when compared to a control. As a result, it has been found that increase in uric acid-induced production of MCP-1 is inhibited by an inhibitor probenecid, but the production of MCP-1 is not inhibited in the presence of an inhibitor probenecid alone.

These results indicate that inhibition of organic anion transportation system in VSMCs makes it possible to block uric acid-induced VSMC proliferation and production of MCP-1, which is noteworthy because it has been considered that an inhibitor such as probenecid or benzbromarone acts as a uricosuric agent by itself in the kidney. However, these results raise an interesting possibility that these inhibitors may become blockers of direct action of uric acid in VSMCs.

Next, the present inventors examined what kinds of organic anion transporters are present in rat VSMCs by RT-PCR. RT-PCR was carried out using rat VSMC total RNA and partial sequences of rat organic anion transporter 1 (OAT1), organic anion transporter 2 (OAT2), organic anion transporter 3 (OAT3), and rat homologue (RST1) of urate anion transporter 1 (URAT1) as primers. As positive controls, rat kidney cells and rat liver cells were used. The photographs of RT-PCR products stained with ethidium bromide are shown in FIGS. 11A to 11D. FIG. 11A shows a 434 bp PCR product obtained using partial sequences of OAT1 as primers, FIG. 11B shows a 462 bp PCR product obtained using partial sequences of OAT2 as primers, FIG. 11C shows a 483 bp PCR product obtained using partial sequences of OAT3 as primers, and FIG. 11D shows a 460 bp PCR product obtained using partial sequences of RST1 as primers. In each of these drawings, the leftmost lane shows a 100 bp ladder (manufactured by Invitrogen Corporation), the rightmost lane shows VSMC, and the middle two lanes show positive controls, kidney (left) and liver (right).

In FIG. 11A, a PCR product was observed only in the lane for kidney. In FIG. 11B, 462 bp bands of PCR products were observed in only the lanes for kidney and liver, and 320 bp bands were observed in all the lanes, but these 320 bp bands were found to be nonspecific as a result of sequence analysis using BLAST. In FIG. 11C, PCR products were observed only in the lanes for kidney and liver. In FIG. 11D, a 460 bp band of a PCR product was observed only in the lane for kidney, and 211 bp bands were observed in all the lanes, but these 211 bp bands were found to be nonspecific as a result of sequence analysis. As described above, expression of these transporters was not confirmed in VSMCs.

Next, RNase protection assay was carried out to evaluate the expression of a voltage-sensitive channel/transporter, UAT (Gene Bank Accession Number: NM 012977). The result is shown in the picture of FIG. 12. In FIG. 12, the leftmost lane shows a probe, the rightmost lane shows liver, and the middle four lanes show VSMC. As a result of RNase protection assay, expression of UAT mRNA was confirmed in rat VSMC and liver. In addition, expression of a housekeeping gene L32 was also confirmed. In FIG. 12, a band in the probe lane is different in size from those in other lanes because the probe contains a polylinker region for probe construction.

Next, the present inventors examined human VSMCs. In order to determine the expression of urate transporter URAT1 in vascular smooth muscle cells (VSMCs) derived from human aorta, RT-PCR (Reverse Transcription PCR) was carried out. The result is shown in the picture of FIG. 13. In FIG. 13, the leftmost and rightmost lanes M show 100 bp DNA ladders, Lane +K contains cDNA from kidney, and Lane −K contains no cDNA from kidney. Lane 0 shows VSMC with no additives, and Lanes 3, 6, 9, and 12 show VSMC stimulated with 3 mg/dL, 6 mg/dL, 9 mg/dL, and 12 mg/dL uric acid, respectively. As a result, the expression of URAT1 in cDNA prepared from VSMCs was confirmed by PCR method irrespective of the presence or absence of uric acid and the concentration of uric acid added.

Further, RT-PCR was performed in the same manner as described above using total RNA isolated from VSMCs derived from human renal afferent arteriole. The result is shown in the picture of FIG. 14. In FIG. 14, the leftmost and rightmost lanes M show 100 bp DNA ladders, Lane +K contains cDNA from kidney, and Lane −K contains no cDNA from kidney. Lane 0 shows VSMC with no additives, and Lanes 3, 6, 9, and 12 show VSMC stimulated with 3 mg/dL, 6 mg/dL, 9 mg/dL, and 12 mg/dL uric acid, respectively.

As a result, the expression of URAT1 in cDNA prepared from VSMCs derived from human renal afferent arteriole was confirmed by PCR method irrespective of the presence or absence of uric acid and the concentration of uric acid added.

Furthermore, RT-PCR was performed in the same manner as described above using total RNA isolated from human umbilical vein epithelial cells (HUVECs). The result is shown in the picture of FIG. 15. In FIG. 15, the leftmost and rightmost lanes M show 100 bp DNA ladders, Lane +K contains cDNA from kidney, and Lane +Endo contains cDNA synthesized from HUVECs. As a result, as in the case of cDNA from kidney, the expression of URAT1 was confirmed by PCR method also in cDNA prepared from HUVECs.

Next, human vascular smooth muscle cells (VSMCs) were homogenized to obtain a cell lysate. Western blot was carried out using the cell lysate and anti-URAT1 antibody. The result is shown in the picture of FIG. 16. In FIG. 16, Lane 0 shows VSMC with no additives, Lanes 3, 6, 9, and 12 show VSMC stimulated with 3 mg/dL, 6 mg/dL, 9 mg/dL, and 12 mg/dL uric acid, respectively, and GAPDH serves as a positive control.

As a result, URAT1 protein was detected using anti-URAT1 antibody in the cell lysate obtained from human VSMCs irrespective of the presence or absence of uric acid and the concentration of uric acid added.

It was impossible to specify from these results a transporter mediating uric acid uptake into rat VSMCs, but the RT-PCR results and the like have shown that a transporter mediating uric acid uptake into human VSMCs is URAT1. It has been already reported that OAT1 and OAT3 mediate uric acid uptake on the basal side of proximal tubule (proximal renal tubule) and that URAT1 plays an important role in uric acid uptake on the luminal side. In addition, it has been already reported that hyperuricemic rat models develop salt-sensitive hypertension, glomerular vascular disorders, and renal disorders (see Non-Patent Documents 1 to 6). The above-described results have shown that a URAT1 inhibitor or blocker is efficacious for healing, preventing or treating such vascular disorders or hypertension, especially vascular disorders or hypertension induced by hyperuricemia. Particularly, it has been shown that uricosuric agents such as probenecid have not only uricosuric effect in kidney but also other effects in VSMCs.

As described above, the present invention has shown that uric acid uptake into vascular smooth muscle cells (VSMCs) is mediated by one of urate transporters, URAT1. Based on recent research findings that vascular disorders, hypertension and renal disorders result from uric acid uptake into vascular smooth muscle cells (VSMCs), especially vascular disorders, hypertension, and renal disorders induced by hyperuricemia result from uric acid uptake into vascular smooth muscle cells (VSMCs), the present invention has shown for the first time that a URAT1 inhibitor or blocker is efficacious for healing, preventing or treating vascular disorders, hypertension, and renal disorders, more specifically vascular disorders, hypertension, and renal disorders induced by hyperuricemia.

Therefore, the present invention provides a medicinal composition for healing, preventing or treating vascular disorders, hypertension, and renal disorders, which comprises a drug having the effect of inhibiting uric acid uptake via URAT1 and a pharmaceutically acceptable carrier. Examples of vascular disorders, hypertension, and renal disorders to which the present invention is suitably applied include disorders induced by hyperuricemia, but are not limited thereto because uric acid is present in blood as a purine metabolite and uric acid uptake into vascular smooth muscle cells (VSMCs) depends on the presence of uric acid in blood. Further, the medicinal composition of the present invention can be used as a preventive, and therefore the present invention provides a medicinal composition to be used as a vascular protective agent.

The drug having the effect of inhibiting uric acid uptake via URAT1 to be used in the present invention is not particularly limited as long as the uric acid uptake level via URAT1 is reduced in the presence of the drug. Examples of such a drug include URAT1 antagonists, URAT1 inhibitors, and URAT1 blockers. More specifically, probenecid and benzbromarone can be mentioned by way of example.

The medicinal composition of the present invention is administered either orally or parenterally, and is formulated into known dosage forms such as tablets, granules, liquid, and injections. For the formulation into such dosage forms, known pharmaceutical additives such as excipients, disintegrators, and stabilizers may be appropriately used.

The effective dose of the active ingredient contained in the medicinal composition of the present invention is appropriately determined by the state of patient's disease or the physical condition of a patient, but is usually an amount enough to eliminate uric acid. For example, the active ingredient of the medicinal composition of the present invention can be administered in an amount of about 1 µg/kg to 50 mg/kg per day.

Further, the present invention also provides a method of healing, preventing or treating vascular disorders, hypertension, and renal disorders, which comprises administering an effective dose of a drug having the effect of inhibiting uric acid uptake via URAT1 to a patient in need of healing, preventing or treating vascular disorders, hypertension, and renal disorders.

Furthermore, the present invention also provides the use of a drug having the effect of inhibiting uric acid uptake via URAT1 to prepare a medicinal composition for healing, preventing or treating vascular disorders, hypertension, and renal disorders.

The present invention also provides a method of screening a substance efficacious for healing, preventing or treating vascular disorders, hypertension, and renal disorders, which comprises using a cell line expressing URAT1 in the presence or absence of a test compound; and assaying the uric acid uptake level. As a cell line expressing URAT1 to be used in the present invention, natural cells such as renal cells and VSMCs may be used, but URAT1 stably expressing cells obtained by introducing URAT1 gene into cells may alternatively be used. More specifically, the present invention provides a method of screening a substance efficacious for healing, preventing or treating vascular disorders, hypertension and renal disorders, which comprises using a cell line expressing URAT; and assaying the uric acid uptake level with the use of a uric acid uptake solution in the presence of a test compound. As a method of assaying the uric acid uptake level to be used in the present invention, a method comprising using uric acid labeled by a radioisotope, such as $^{14}$C-uric acid can be mentioned by way of example.

The uric acid to be used in this method may be uric acid itself, but alternatively urate such as a sodium may be used.

Moreover, the present invention also provides a method of screening a substance efficacious for healing, preventing or treating vascular disorders, hypertension, and renal disorders, which comprises using a cell line expressing URAT1 in the presence or absence of a test compound; and assaying the proliferation ability of the cells. As a cell line expressing URAT1 to be used in this method, cells capable of proliferating in the presence of uric acid or urate are preferably used. More specifically, the present invention provides a method of screening a substance efficacious for healing, preventing or treating vascular disorders, hypertension, and renal disorders, which comprises using a cell line expressing URAT1; and assaying the thymidine uptake level by the cells with the use of a uric acid uptake solution containing thymidine and a test compound. As a method of assaying the thymidine uptake level, a method comprising using thymidine labeled by a radioisotope, such as $^{3}$H-thymidine can be mentioned by way of example.

The uric acid to be used in this method may be uric acid itself, but alternatively a sodium salt of uric acid may be used.

Moreover, the present invention also provides a method of screening a substance efficacious for healing, preventing or treating vascular disorders, hypertension, and renal disorders, which comprises using a cell line expressing URAT1 in the presence or absence of a test compound; and assaying the amount of a monocyte chemotactic factor produced by the cells. As a cell line expressing URAT1 to be used in this method, cells capable of producing a monocyte chemotactic factor such as MCP-1 in the presence of uric acid or urate are preferably used. More specifically, the present invention provides a method of screening a substance efficacious for healing, preventing or treating vascular disorders, hypertension, and renal disorders, which comprises using a cell line expressing URAT1 and assaying the amount of a monocyte chemotactic factor, such as MCP-1, produced by the cells with the use of a uric acid uptake solution in the presence of a test compound. As a method of assaying the amount of a monocyte chemotactic factor such as MCP-1 produced by the cells, ELISA can be mentioned by way of example.

The uric acid to be used in this method may be uric acid itself, but alternatively urate such as a sodium may be used.

It is to be noted that the activity of active ingredient of the medicinal composition according to the present invention can be determined using hypertensive animal models such as spontaneously-hypertensive rat models (SHR).

Effect of the Invention

The present invention has shown, for the fist time, the conditions for uric acid uptake into vascular smooth muscle cells (VSMCs) and the mechanism of uric acid uptake into VSMCs. The present invention has shown that URAT1 plays an important role as a urate transporter in smooth muscle cells when uric acid in blood is transported into the smooth muscle cells, and that URAT1 is present also in vascular smooth muscle cells and participates in transportation of uric acid from blood to smooth muscle cells, and that such action plays an important role in the development of morbid conditions such as hypertension and vascular lesions induced by hyperuricemia. These findings have revealed that uric acid in vascular smooth muscle cells that induces various vascular disorders, disorders of various organs such as kidney and liver, and hypertension is taken up by vascular smooth muscle cells via URAT1. Therefore, according to the present invention, it is possible to provide a medicinal composition for healing, preventing or treating vascular disorders, hypertension, and renal disorders, which comprises a drug having the effect of inhibiting uric acid uptake via URAT1; and a pharmaceutically acceptable carrier.

Further, according to the present invention, it is also possible to provide a novel method of screening a substance efficacious for healing, preventing or treating vascular disorders, hypertension, and renal disorders, which comprises using a cell line expressing URAT1 such as a cell line stably expressing URAT1 gene in the presence or absence of a test compound; and assaying the uric acid uptake level, the proliferation ability of the cells and/or the amount of a monocyte chemotactic factor produced by the cells. The screening method according to the present invention makes it possible to develop a novel antihypertensive and a novel drug that exerts a vascular protective effect by inhibiting blood vessel degeneration.

BRIEF DESCRIPTION OF THE DRAWINGS

FIG. 11A shows the case using partial sequences of OAT1, FIG. 11B shows the case using partial sequences of OAT2, FIG. 11C shows the case using partial sequences of OAT3 and FIG. 11D shows the case using partial sequences of URAT1, respectively. The leftmost lane shows a 100 bp ladder (manufactured by Invitrogen Corporation), the rightmost lane shows VSMC, and the middle two lanes show positive controls, rat kidney cells (left) and rat liver cells (right).

Hereinbelow, the present invention will be described in more detail with reference to the following Examples, but the present invention is not limited thereto.

In the following experiments, vascular smooth muscle cells (VSMCs) derived from rat aorta were used (see Zhang S, Yang Y, et al., Circulation., 2003; 107, 1539-44). These cells were cultured in Dulbecco's Modified Eagle Medium (DMEM, GIBCO) containing 10% fetal bovine serum (FBS), 1% glutamine, and 1% penicillin/streptomycin solution (100 units/ml penicillin, 100 μg/mL streptomycin; GIBCO). The cultured VSMCs were transferred into wells of a 35-mm six-well culture plate (NUNC), and were then maintained at 37° C. in an atmosphere of 5% carbon dioxide and 95% air in a humidified tissue culture incubator. The culture medium was replaced every 2 days. The VSMCs used in the experiments were 5th to 12th generation cells.

It is to be noted that the entire disclosure of Japanese Patent Application No. 2003-384863 is incorporated herein by reference.

EXAMPLE 1

Uptake of $^{14}C$-Urate

Figure 3:
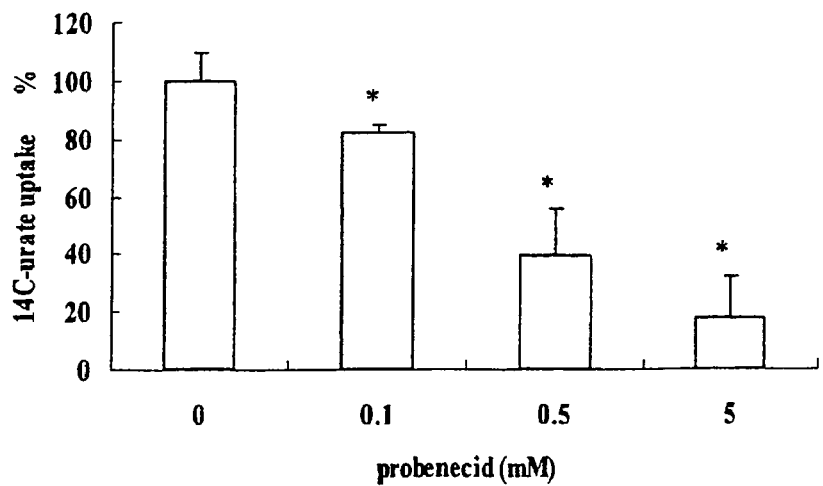
FIG. 3 is a graph which shows the result of a test carried out to examine the effect of probenecid on inhibition of $^{14}$C-urate uptake into rat VSMCs, in which a vertical axis represents the ratio (%) of $^{14}$C-urate uptake level determined when the $^{14}$C-urate uptake level in the absence of probenecid is defined as 100%, and a horizontal axis represents the concentration of probenecid (mM).
Figure 4:
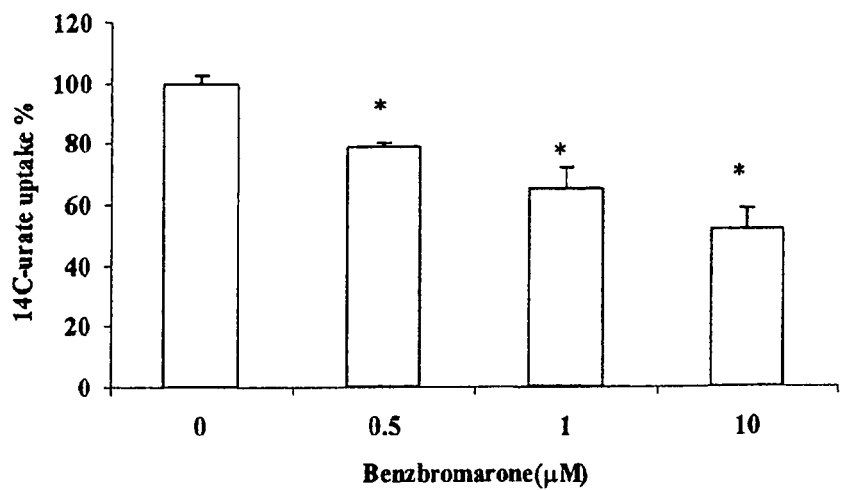
FIG. 4 is a graph which shows the result of a test carried out to examine the effect of benzbromarone on inhibition of $^{14}$C-urate uptake into rat VSMCs, in which a vertical axis represents the ratio (%) of $^{14}$C-urate uptake level determined when the $^{14}$C-urate uptake level in the absence of benzbromarone is defined as 100%, and a horizontal axis represents the concentration of benzbromarone (μM).

The VSMCs ($4 \times 10^5$ cells) were transferred into wells of a six-well culture plate together with 10% FBS-DMEM. After a lapse of one day, the VSMCs were placed in DMEM medium without serum and incubated over night to stop growth. In all the experiments, cells and all the solutions used were maintained at 37° C. The VSMCs were cultured with 8-$^{14}C$-urate (20 μM final concentration) (manufactured by American Radiolabeled Chemicals, Inc. (St. Louis, Mo.), specific activity: 50 μCi/mmol) in the presence or absence of various inhibitors. Incubation of the VSMCs was terminated after 5 minutes to stop uptake of $^{14}C$-urate slightly early. The result is shown in FIGS. 3 and 4.

Figure 2:
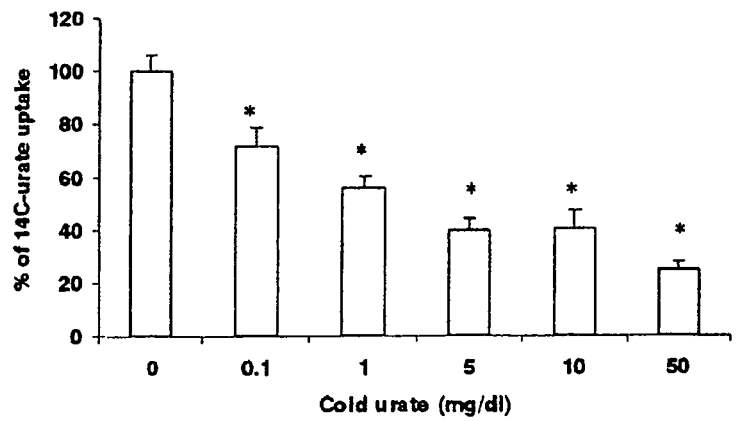
FIG. 2 is a graph which shows the result of a test carried out to examine the competition between $^{14}$C-urate and cold urate for uptake by rat VSMCs, in which a vertical axis represents the ratio (%) of $^{14}$C-urate uptake level determined when the $^{14}$C-urate uptake level in the absence of cold urate is defined as 100%, and a horizontal axis represents the concentration of cold urate (mg/dL).
Figure 5:
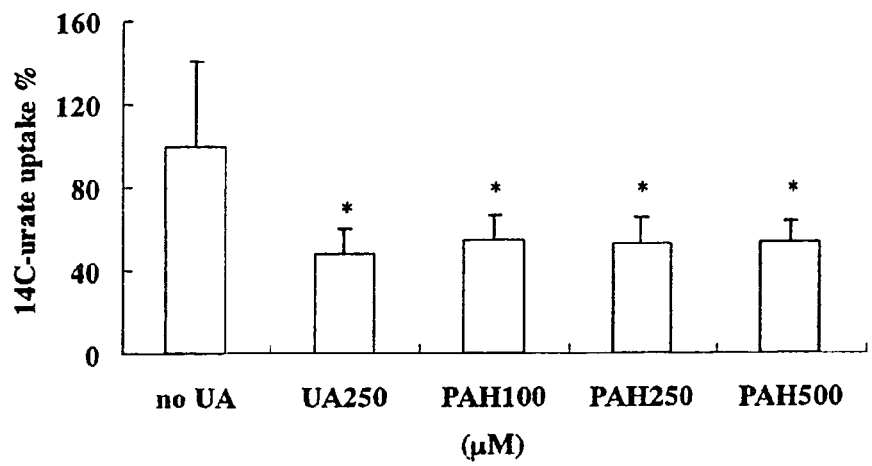
FIG. 5 is a graph which shows the result of a test carried out to examine the competition between $^{14}$C-urate and para-amino hippurate (PAH) for uptake by rat VSMCs, in which a vertical axis represents the ratio (%) of $^{14}$C-urate uptake level determined when the $^{14}$C-urate uptake level in the absence of PAH is defined as 100%, and a horizontal axis represents the concentration of PAH (μM).
Figure 6:
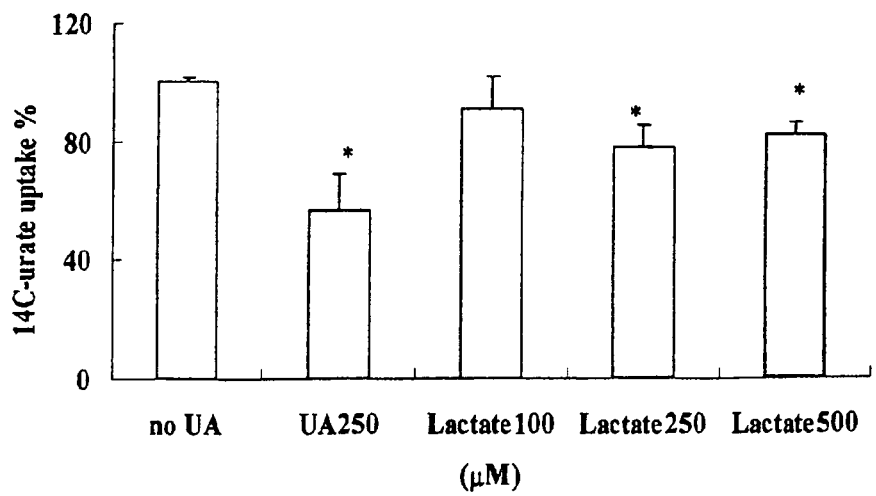
FIG. 6 is a graph which shows the result of a test carried out to examine the competition between $^{14}$C-urate and lactate for uptake by rat VSMCs, in which a vertical axis represents the ratio (%) of $^{14}$C-urate uptake level determined when the $^{14}$C-urate uptake level in the absence of lactate is defined as 100%, and a horizontal axis represents the concentration of lactate (μM).

Some other experiments were carried out to examine uptake of radioisotope-labeled urate by the VSMCs in the presence of another organic anion such as cold urate, lactate or para-amino hippurate (PAH) or in the presence of an organic anion transporter inhibitor (probenecid or benzbromarone). In these experiments, uptake was stopped by rapidly aspirating the media, and the cells were immediately washed with ice-cooled PBS three times. Blank values were subtracted from all values of the culture solutions rapidly aspirated and cells washed in such a manner described above. Then, the cells were lysed for 15 minutes in 1 mL of 1N NaOH to obtain a cell lysate. 0.5 mL of the cell lysate was added to 5 mL of BCS scintillation fluid (manufactured by Amersham) to measure the amount of 8-$^{14}C$-urate accumulated in the cells. Radioactivity was measured in a liquid scintillation counter. The 8-$^{14}C$-urate uptake level by the cells is expressed as total cpm/well or as a percentage (%) with respect to a control. The result is shown in FIGS. 2, 5, and 6.

Further, in still another experiment, urate uptake was examined under polarized or depolarized conditions to determine whether urate uptake was voltage sensitive. The conditions for the experiment were the same as described above except that a culture solution for polarized conditions and a culture solution for depolarized conditions were different. More specifically, after 12 hour starvation, the serum free medium was removed and replaced with 0.45 mL of HEPES-physiological saline solution (PSS) containing 140 mM NaCl, 4 mM KCl, 2 mMCaCl$_2$, 1 mM MgCl$_2$, 5 mM glucose, and 16 mM HEPES-tris (pH 7.4) for polarized conditions, or 100 mM-KCl uptake solution containing 44 mM NaCl, 100 mM KCl, 2 mM CaCl$_2$, 1 mM MgCl$_2$, 5 mM glucose, and 16 mM HEPES-tris (pH 7.4) for depolarized conditions.

Figure 1:
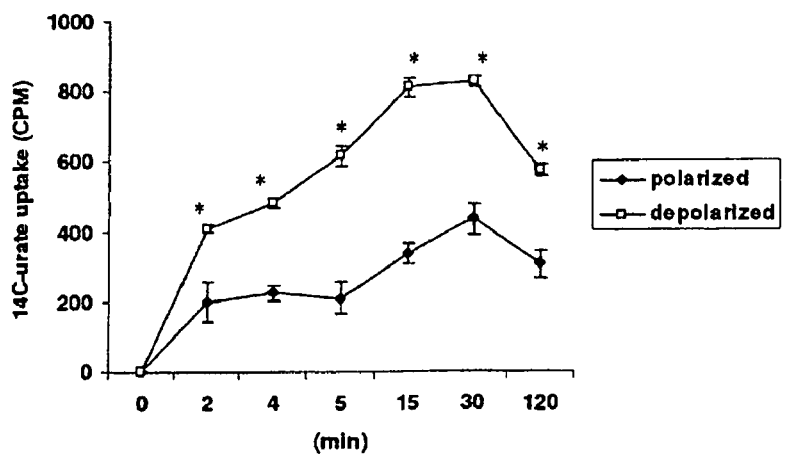
FIG. 1 is a graph which shows the result of a test carried out to examine urate uptake into rat vascular smooth muscle cells (VSMCs) under polarized or depolarized conditions, in which a vertical axis represents the $^{14}$C-urate uptake (CPM) level, a horizontal axis represents time (min), the symbol "☐" represents a case where urate uptake was examined under depolarized conditions, and the symbol "◆" represents a case where urate uptake was examined under polarized conditions.

The result is shown in FIG. 1.

EXAMPLE 2

VSMC Proliferation Test

Figure 7:
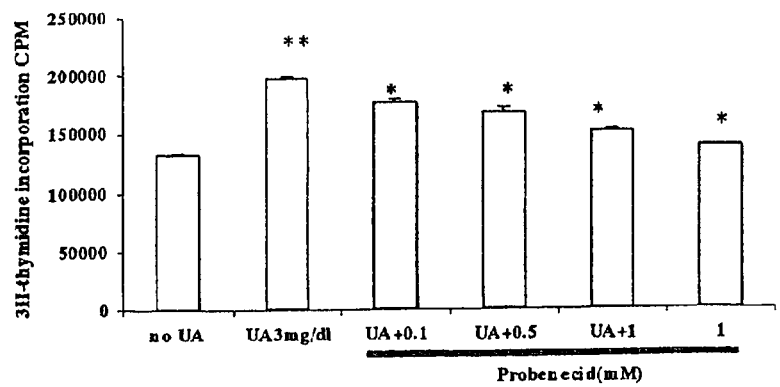
FIG. 7 is a graph which shows the result of a test carried out to measure the $^3$H-thymidine uptake level by rat VSMCs to assay rat VSMC proliferation after 24 hour incubation, in which a vertical axis represents the $^3$H-thymidine uptake level by rat VSMCs (CPM), and a horizontal axis represents cases where no uric acid is present (no UA), 3 mg/dL uric acid is present (UA), 3 mg/dL uric acid and 0.1, 0.5, or 1 mM probenecid are present (UA+0.1 etc), and probenecid is present alone (1).
Figure 8:
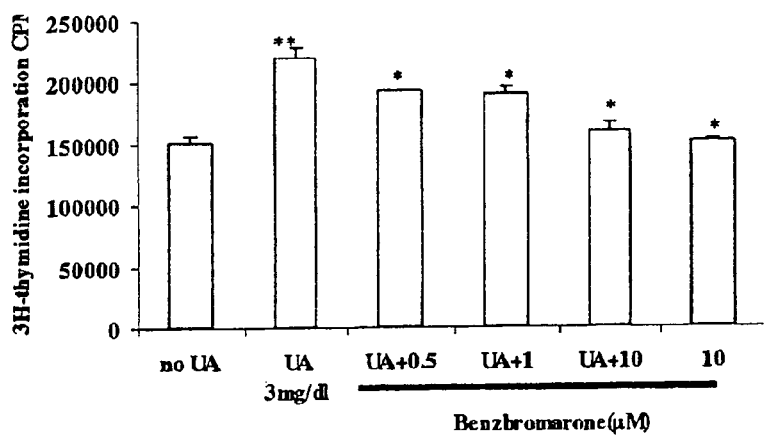
FIG. 8 is a graph which shows the result of a test carried out to measure the $^3$H-thymidine uptake level by rat VSMCs to assay rat VSMC proliferation after 24 hour incubation, in which a vertical axis represents the $^3$H-thymidine uptake level by rat VSMCs (CPM), and a horizontal axis represents cases where no uric acid is present (no UA), 3 mg/dL uric acid is present (UA), 3 mg/dL uric acid and 0.5, 1 or 10 μM benzbromarone are present (UA+0.5 etc), and benzbromarone is present alone (10).
Figure 9:
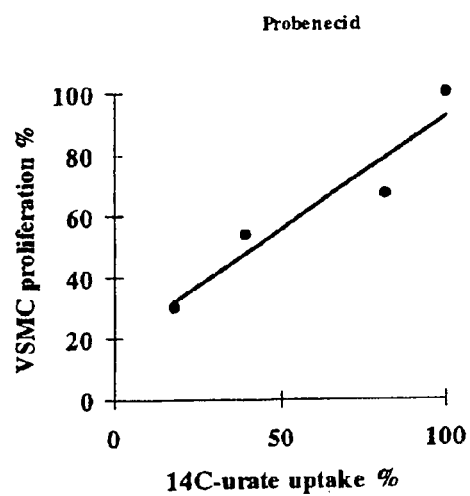
FIG. 9 is a graph which shows a result obtained by making a comparison between the ratio (%) of VSMC proliferation inhibition by an organic anion transportation inhibitor, probenecid after 24 hour incubation and the ratio (%) of uric acid uptake inhibition by probenecid within 5 minutes, in which a vertical axis represents the ratio of VSMC proliferation inhibition and a horizontal axis represents the ratio of uric acid uptake inhibition.

The VSMCs ($4 \times 10^5$ cells) were transferred into wells of a six-well culture plate together with 10% FBS-DMEM, and were cultured for 24 hours. Then, the cells were starved for 48 hours in 0.5% FBS-DMEM, and the resting VSMCs were stimulated with 3 mg/dL uric acid containing 1 μCi $^3H$-thymidine to detect DNA synthesis. Further, 2 μCi/mL $^3H$-thymidine was added to each well 2 hours before harvesting the cells. The cells were washed with ice-cooled PBS three times, and were lysed in 1 mL of 1N NaOH. 0.5 mL of the cell lysate was added to 5 mL of scintillation fluid to measure the $^3H$-thymidine uptake level by the cells. The $^3H$-thymidine uptake level by the cells was expressed as CMP/well and counted in a liquid scintillation counter. Some experiments were carried out in the presence of different concentrations of probenecid or benzbromarone (organic anion transporter inhibitor). The result is shown in FIGS. 7 and 8.

In the same manner as described above, VSMC proliferation was evaluated using organic anions (lactate and PAH).

EXAMPLE 3

ELISA of MCP-1 Protein

Figure 10:
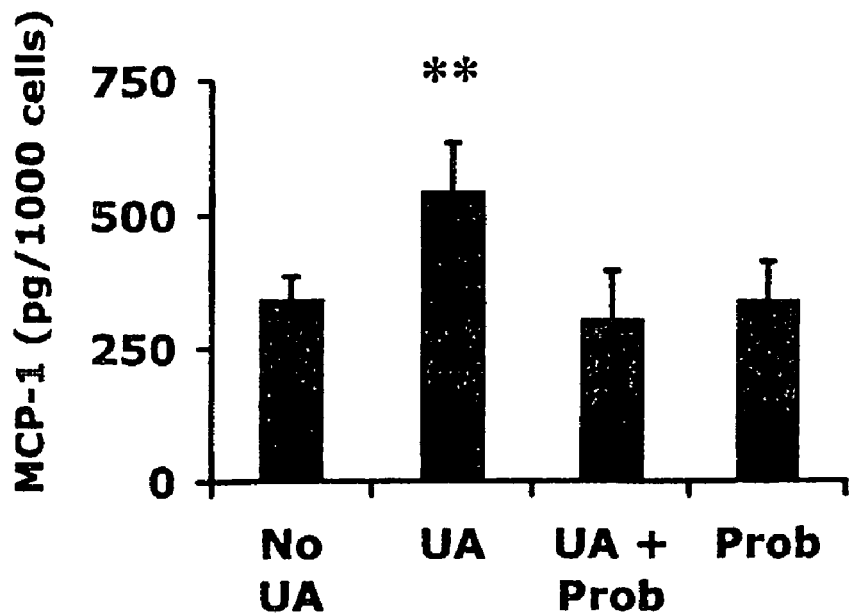
FIG. 10 is a graph which shows the result of ELISA carried out to measure the amount of MCP-1 secreted into culture supernatant of rat VSMCs after 24 hour incubation, in which a vertical axis represents the amount of MCP-1 (pg/1000 cells) and a horizontal axis represents cases where nothing is present (No UA), 3 mg/dL uric acid is present (UA), 3 mg/dL uric acid and 1 mM probenecid are present (UA+Prob), and probenecid is present alone (Prob).

The VSMCs ($5 \times 10^4$ cells/well) were placed in wells of a 24-well plate, and serum was deprived after reaching 70% confluence. Then, media with or without 3 mg/dL uric acid was added and the cells were cultured for 24 hours in the presence or absence of 1 mM probenecid. The amount of MCP-1 protein contained in supernatant was measured by ELISA (OptEIA MCP-1 set, BD Pharmingen), and corrected for cell number. Each experiment was repeated three times. The result is shown in FIG. 10.

EXAMPLE 4

Detection of OAT Transporter by RT-PCR

Total RNA was prepared from rat VSMCs using RNeasy RNA purification kit (Qiagen, Valencia, Calif.). Poly (A) $^+$RNA was isolated using Oligotex mRNA purification system (Qiagen), and reverse transcription was performed using random primers in one-step RT reaction. Kidney poly (A) $^+$RNA and liver poly (A) $^+$RNA available from Clontech (Palo Alto, Calif.) were used as positive controls. A negative control reaction was carried out by heat inactivation of reverse transcriptase prior to addition of primers to ensure the absence of DNA contamination. PCR reactions were carried out using the following nucleotide sets.

```
OAT1:
784-810                                    (SEQ ID NO: 1)
5'-CTGTGCAGCCTATGCACCCAACTATAC-3'

1218-1190 (antisense strand)               (SEQ ID NO: 2)
5'-CCTTTGCTTAGAGTCAGTTCCTTCTGCAG-3'

OAT2:
642-672                                    (SEQ ID NO: 3)
5'-CCATCAACTACATCATGTTCGTAGTCACCCG-3'

1105-1076 (antisense strand)               (SEQ ID NO: 4)
5'-GATATGTCGGAGCTGAGATGTTCGGAACAG-3'

OAT3:
437-465                                    (SEQ ID NO: 5)
5'-GAGACACCATTGTGATAGAGTGGGACTTG-3'
```

-continued 920-889 (antisense strand) (SEQ ID NO: 6)
5'-GATAGAACCAGCCAGCGTATGGACTCTGGTAC-3'

RST1 (mouse homologue of URAT1)
377-405 (SEQ ID NO: 7)
5'-CATCTTATGCTTATCCGGGACAAGTCCTC-3'

768-739 (antisense strand) (SEQ ID NO: 8)
5'-GAGTCTGTTGAAGAGGGTAGAGCAGTCTAC-3'

Figure 11:
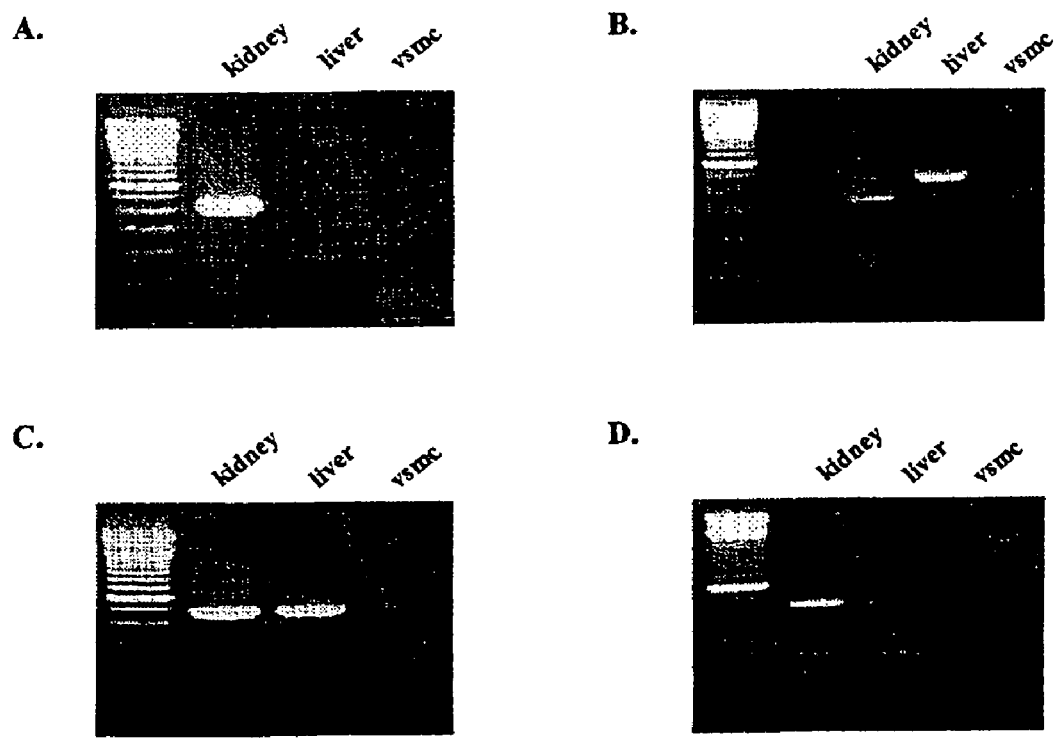
FIGS. 11A to 11D are photographs of ethidium bromide-stained PCR products obtained by carrying out RT-PCR using rat VSMC total RNA and partial sequences of rat organic anion transporter 1 (OAT1), organic anion transporter 2 (OAT2), organic anion transporter 3 (OAT3), and urate anion transporter 1 (URAT1) as primers, respectively. Rat kidney and liver cells were used as positive controls.

RT-PCR reactions were carried out using Ready-To-Go RT-PCR beads (Amersham). First strand cDNA was synthesized using pd(N)$_6$ at 42° C. for 15 minutes. PCR conditions were initial denaturation at 95° C. for 5 min, followed by 32 cycles of denaturation at 95° C. for 30 sec, annealing at 55° C. for 30 sec, and extension at 72° C. for 1 min. Samples were stored at 4° C. PCR products were separated by electrophoresis on 1.5% agarose gel, and bands of appropriate molecular weights were excised from the gel, purified using a QIA quick gel extraction kit (QIAGEN), and subcloned into TOPO TA cloning vector (Invitrogen Corporation). The vector was digested with an restriction enzyme EcoRI, and sequenced by dye terminator method using Applied Biosystem Sequencer (ABI3730). The integrity of poly(A)mRNA was evaluated by amplification of GADPH mRNA using the following primer set: sense primer (5'-ACCCCCAATGTATCCGTTGT-3' (SEQ ID NO: 9)) and antisense primer (5'-TACTCCTTG-GAGGCCATGTA-3' (SEQ ID NO: 10)). The result is shown in FIG. 11.

EXAMPLE 5

RNase Protection Assay (RPA)

RNase protection assay (RPA) was performed on 2 to 4 µg of RNA using RPAsI kit (Torrey Pines Biolab, Houston, Tex.). A nucleotide sequence of 325 bp from the 5' end to 325 of rat UAT (Gene Bank Accession Number: NM012977) was subcloned into pcDNA-UAT-EGFP. This plasmid was digested with BamHI and EcoRI and ligated to a plasmid pBluescript to obtain a plasmid named pBS-UAT-325. The plasmid was digested with BamHI to linearize it, and riboprobe (RNA probe) was synthesized using T7RNA polymerase in the presence of α-$^{32}$P[UTP].

Figure 12:
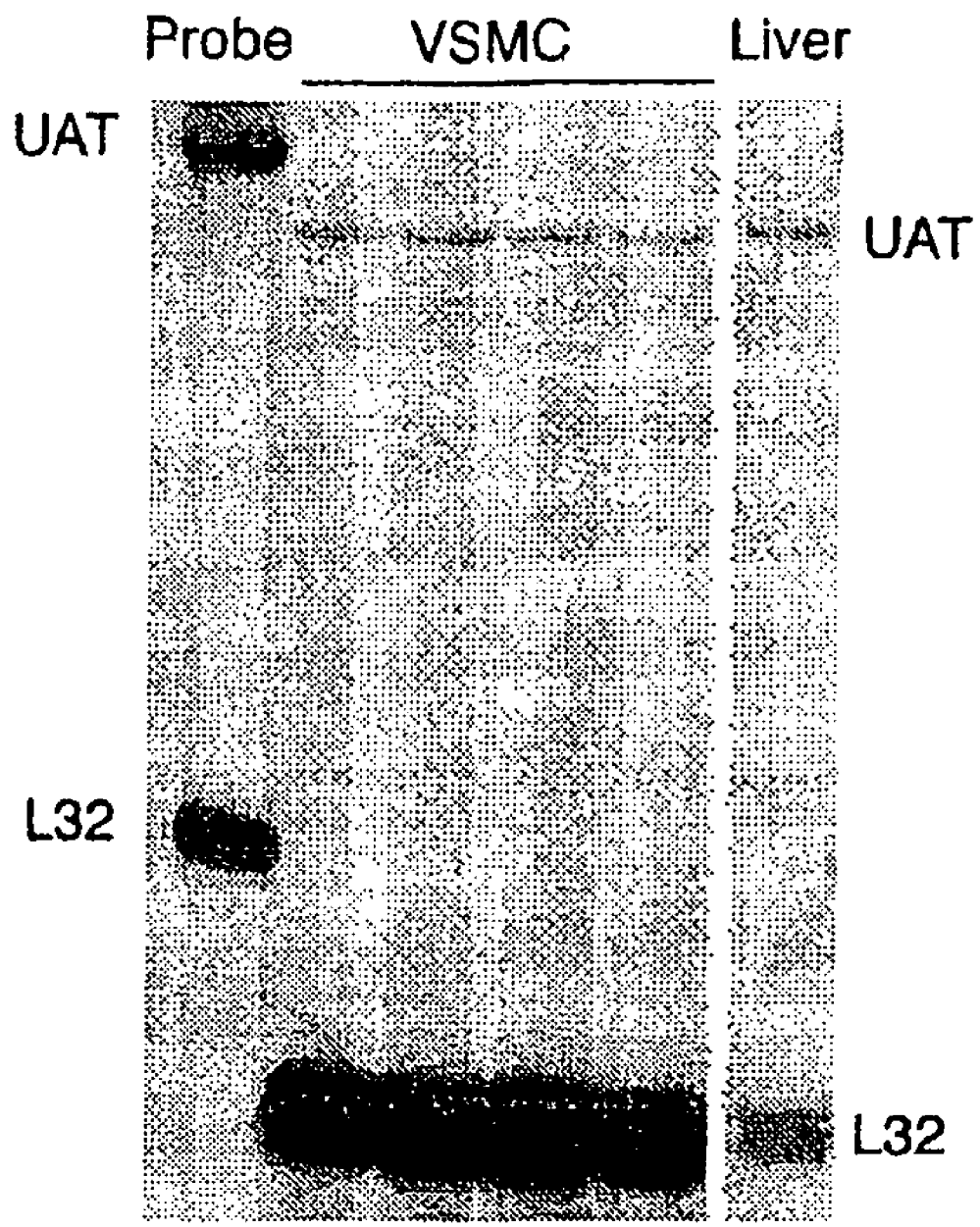
FIG. 12 is a graph which shows the result of RNase protection assay carried out to evaluate the expression of UAT (Gene Bank Accession Number: NM 012977), in which the leftmost lane shows a probe, the rightmost lane shows liver, and middle four lanes show VSMC.

The result is shown in FIG. 12.

EXAMPLE 6

Total RNA isolated from vascular smooth muscle cells (VSMCs) derived from human aorta was reverse transcribed to synthesize cDNA. PCR was performed using the cDNA and partial sequences of urate transporter URAT1 as primers.

Figure 13:
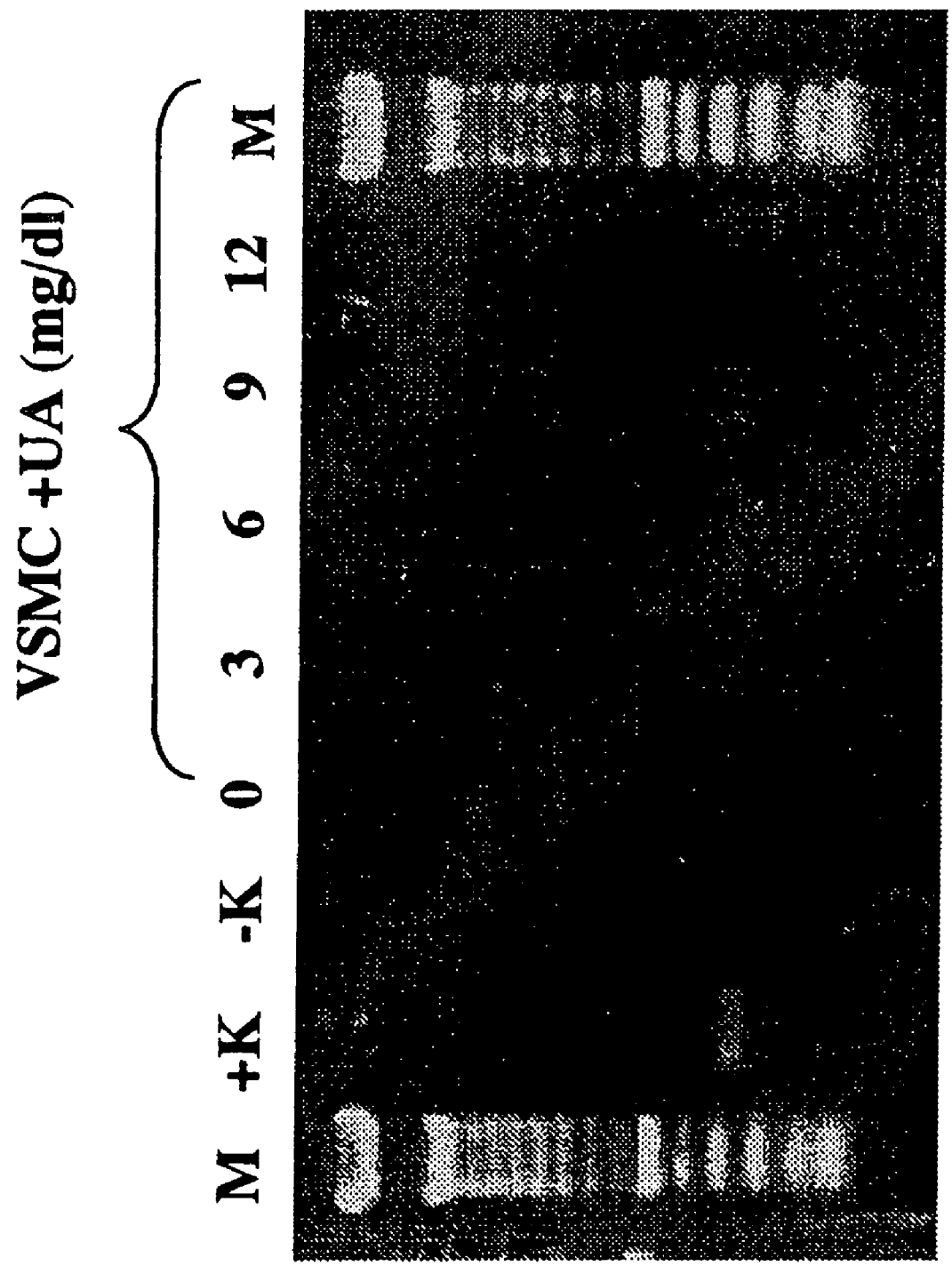
FIG. 13 is a photograph which shows the result of RT-PCR carried out to determine the expression of urate transporter URAT1 in vascular smooth muscle cells (VSMCs) derived from human aorta.

The result is shown in FIG. 13. In FIG. 13, the leftmost and rightmost lanes M show 100 bp DNA ladders, Lane +K contains cDNA from kidney, and Lane −K contains no cDNA from kidney. Lane 0 shows VSMC with no additives, and Lanes 3, 6, 9, and 12 show VSMC stimulated with 3 mg/dL, 6 mg/dL, 9 mg/dL, and 12 mg/dL uric acid, respectively.

As a result, the expression of URAT1 in cDNA prepared from VSMCs was confirmed by PCR method irrespective of the presence or absence of uric acid and the concentration of uric acid added.

EXAMPLE 7

PCR was performed in the same manner as in the Example 6 except that total RNA isolated from vascular smooth muscle cells derived from human renal afferent arteriole was used.

Figure 14:
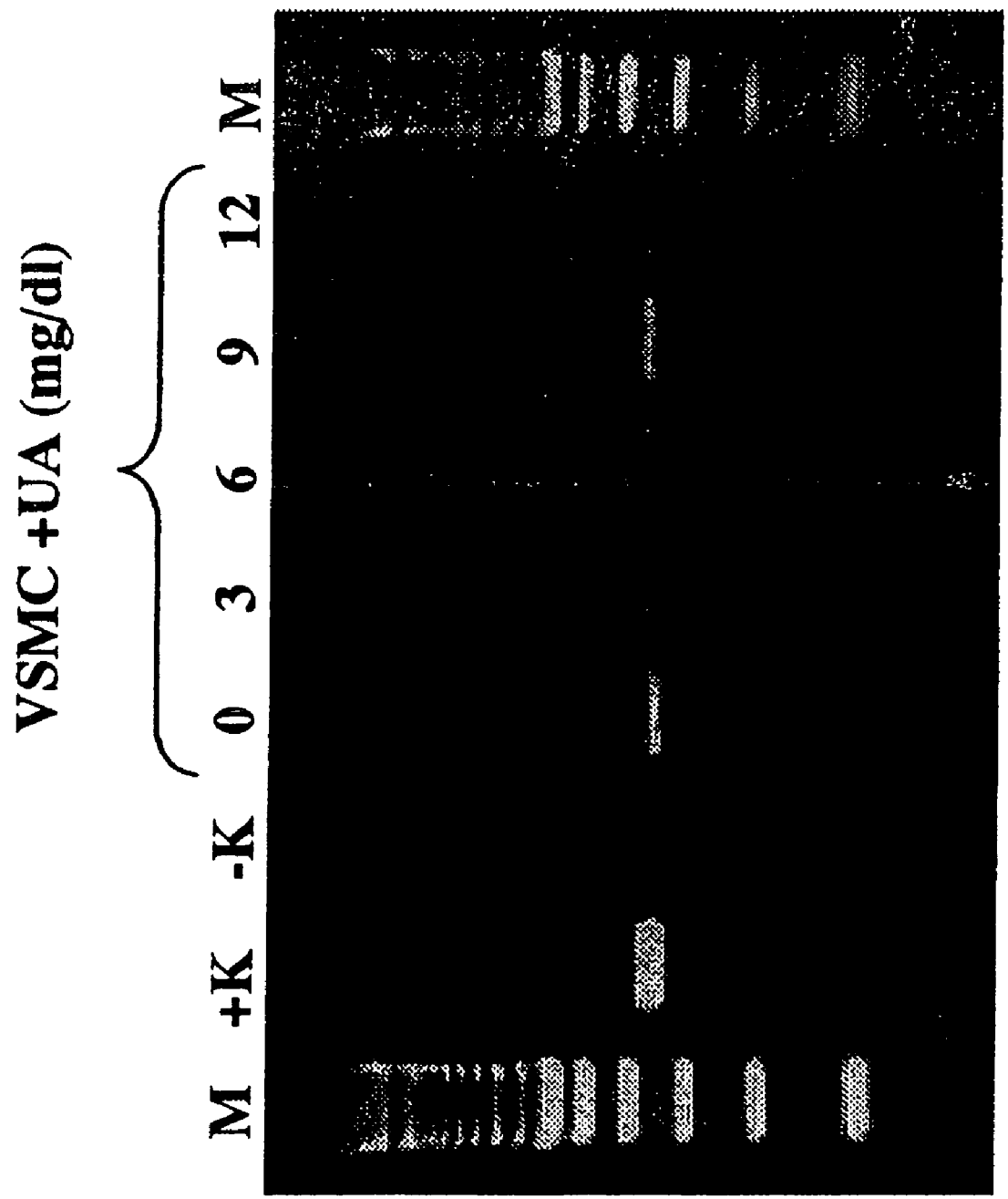
FIG. 14 is a photograph which shows the result of RT-PCR carried out to determine the expression of urate transporter URAT1 in vascular smooth muscle cells (VSMCs) derived from human renal afferent arteriole.

The result is shown in FIG. 14. In FIG. 14, the leftmost and rightmost lanes M show 100 bp DNA ladders, Lane +K contains cDNA from kidney, and Lane −K contains no cDNA from kidney. Lane 0 shows VSMC with no additives, and Lanes 3, 6, 9, and 12 show VSMC stimulated with 3 mg/dL, 6 mg/dL, 9 mg/dL, and 12 mg/dL uric acid, respectively.

As a result, the expression of URAT1 in cDNA prepared from VSMCs was confirmed by PCR method irrespective of the presence or absence of uric acid and the concentration of uric acid added.

EXAMPLE 8

PCR was performed in the same manner as in the Example 6 except that total RNA isolated from human umbilical vein epithelial cells (HUVECs) was used.

Figure 15:
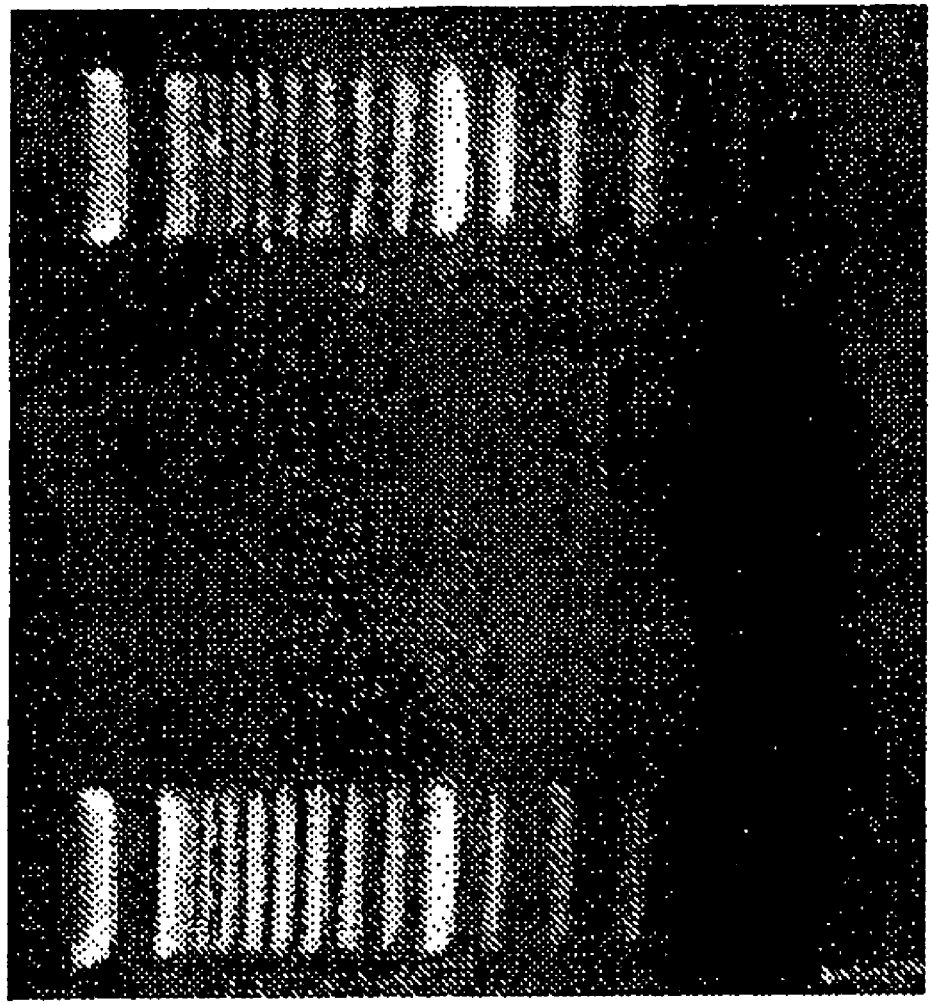
FIG. 15 is a photograph which shows the result of RT-PCR carried out to determine the expression of urate transporter URAT1 in human umbilical vein epithelial cells (HUVECs).

The result is shown in FIG. 15. In FIG. 15, the leftmost and rightmost lanes M show 100 bp DNA ladders, Lane +K contains cDNA from kidney, and Lane +Endo contains cDNA synthesized from HUVECs. As a result, as in the case of cDNA from kidney, the expression of URAT1 was confirmed by PCR method also in cDNA prepared from HUVECs.

EXAMPLE 9

Human vascular smooth muscle cells (VSMCs) were homogenized to obtain a cell lysate. Western blot was performed using the cell lysate and anti-URAT1 antibody. GAPDH was used as a positive control.

Figure 16:
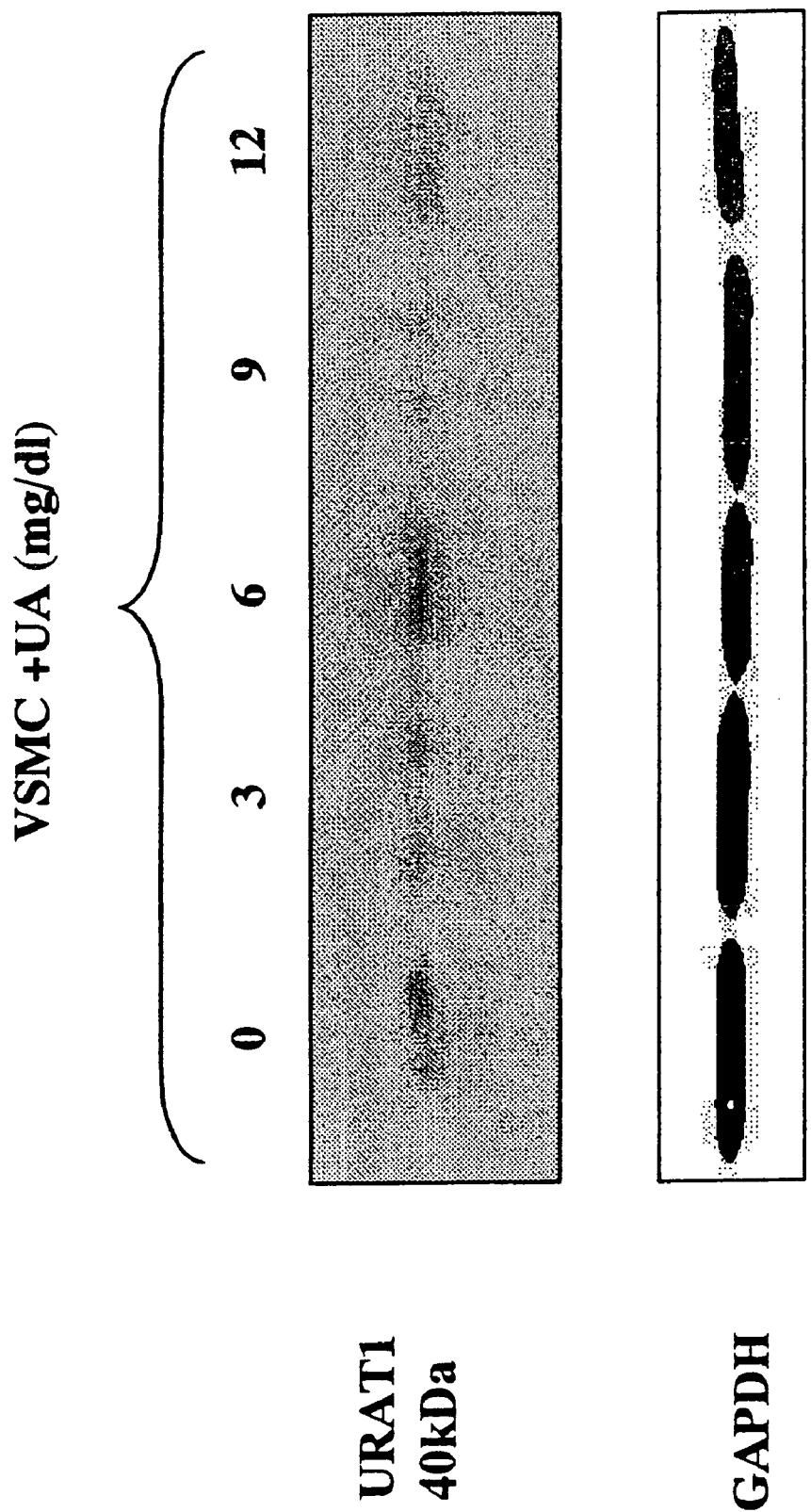
FIG. 16 is a photograph which shows the result of Western blot carried out to determine the expression of urate transporter URAT1 in human vascular smooth muscle cells (VSMCs).

The result is shown in FIG. 16. In FIG. 16, Lane 0 shows VSMC with no additives, Lanes 3, 6, 9, and 12 show VSMC stimulated with 3 mg/dL, 6 mg/dL, 9 mg/dL, and 12 mg/dL uric acid, respectively, and GAPDH serves as a positive control.

As a result, URAT1 protein was detected using anti-URAT1 antibody in the cell lysate prepared from human VSMCs irrespective of the presence or absence of uric acid and the concentration of uric acid added.

Industrial Applicability

According to the present invention, it is possible to provide a novel medicinal composition for healing, preventing or treating various vascular disorders and hypertension resulting from uric acid. Further, according to the present invention, it is also possible to provide a novel method of screening an active ingredient of the medicinal composition for a remedy, preventive or treating by focusing attention on the function of one of urate transporters, URAT1. This screening method allows development of a novel antihypertensive and a novel drug that exerts a vascular protective effect by inhibiting blood vessel degeneration.

Sequence Listing Free Text

SEQ ID NO. 1 is a forward primer for detecting OAT1.
SEQ ID NO. 2 is a reverse primer for detecting OAT1.
SEQ ID NO. 3 is a forward primer for detecting OAT2.
SEQ ID NO. 4 is a reverse primer for detecting OAT2.
SEQ ID NO. 5 is a forward primer for detecting OAT3.
SEQ ID NO. 6 is a reverse primer for detecting OAT3.
SEQ ID NO. 7 is a forward primer for detecting RST1.
SEQ ID NO. 8 is a reverse primer for detecting RST1.

The invention claimed is:

1. A method of screening a substance efficacious for healing or treating a vascular disorder resulting from abnormal uric acid uptake into a vascular smooth muscle cell or abnormal uric acid elimination by URAT1 from a vascular smooth muscle cell, wherein the method comprises:
   a. contacting a vascular smooth muscle cell with a test compound and urate;
   b. measuring the amount of uric acid in i) the vascular smooth muscle cell, or ii) a medium comprising the vascular smooth muscle cell;
   c. comparing the amount of uric acid with a control, wherein the control is i) the level of uric acid in a control vascular smooth muscle cell, or ii) the level of uric acid in a medium comprising the control vascular smooth muscle cell, respectively; and
   d. identifying the test compound as efficacious for healing, preventing or treating a vascular disorder when addition of the test compound increases or decreases the amount of uric acid in the vascular smooth muscle cell or intercellular in the medium comprising the vascular smooth muscle cell, as compared with the control.

2. The method according to claim 1, wherein the cell is an umbilical vein endothelial cell.

3. The method of claim 1, wherein the method further comprises identifying the test compound as a uric acid uptake inhibiting substance when i) the amount of uric acid in the vascular smooth muscle cell is increased as compared to the control, or ii) the amount of uric acid in the medium comprising the vascular smooth muscle cell is decreased as compared to the control.

4. The method of claim 3, wherein the method further comprises identifying the test compound as a uric acid uptake promoting substance when i) the amount of uric acid in the vascular smooth muscle cell is decreased as compared to the control, or ii) the amount of uric acid in the medium comprising the vascular smooth muscle cell is increased as compared to the control.

* * * * *